(12) United States Patent
Sukawa

(10) Patent No.: US 8,663,578 B2
(45) Date of Patent: Mar. 4, 2014

(54) TANK FOR INTRODUCING LIQUID DROP THEREINTO AND ANALYZING DEVICE

(75) Inventor: Yukihiro Sukawa, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 406 days.

(21) Appl. No.: 12/937,432

(22) PCT Filed: Mar. 30, 2009

(86) PCT No.: PCT/JP2009/056504
§ 371 (c)(1),
(2), (4) Date: Oct. 12, 2010

(87) PCT Pub. No.: WO2009/130977
PCT Pub. Date: Oct. 29, 2009

(65) Prior Publication Data
US 2011/0023635 A1    Feb. 3, 2011

(30) Foreign Application Priority Data
Apr. 25, 2008   (JP) .................. 2008-115480

(51) Int. Cl.
*B01L 3/00* (2006.01)
*G01N 33/52* (2006.01)
*G01N 31/22* (2006.01)

(52) U.S. Cl.
USPC ........... 422/502; 422/503; 422/504; 422/421; 422/425

(58) Field of Classification Search
USPC ......... 422/502–504, 551–554, 559, 402, 407, 422/420–421, 425; 73/864.83
See application file for complete search history.

(56) References Cited

U.S. PATENT DOCUMENTS

| | | | |
|---|---|---|---|
| 6,540,962 B1 * | 4/2003 | Okubo et al. | 422/401 |
| 7,274,016 B2 | 9/2007 | Iida et al. | |
| 7,517,499 B2 | 4/2009 | Kahl | |
| 7,569,381 B2 * | 8/2009 | Aoyagi | 435/287.2 |
| 8,075,852 B2 * | 12/2011 | Gao et al. | 422/502 |
| 2006/0177347 A1 | 8/2006 | Larsen et al. | |

FOREIGN PATENT DOCUMENTS

| | | |
|---|---|---|
| JP | 8-313410 | 11/1996 |
| JP | 2003-302399 | 10/2003 |
| JP | 2005-504317 | 2/2005 |
| JP | 2006-349347 | 12/2006 |
| JP | 2006-349594 | 12/2006 |
| JP | 2007-78490 | 3/2007 |
| WO | WO 03/104771 | 12/2003 |
| WO | WO 2004/51229 | 6/2004 |

* cited by examiner

*Primary Examiner* — Brian R Gordon
(74) *Attorney, Agent, or Firm* — Fox Rothschild LLP

(57) ABSTRACT

A liquid droplet introducing tank 3A includes a tank body 31, which is formed by mutually opposing top surface 31a and bottom surface 31b, and a side surface 31c. The tank also includes an injection hole 32 that is opened in the top surface 31a. Liquid droplets Dr are injected from the injection hole 32. The center of the injection hole 32 is closer to the side surface 31c than the center of the top surface 31a. The liquid droplet introducing tank 3A enables liquid droplets to be suitably injected therein and is suitable for reducing size.

9 Claims, 26 Drawing Sheets

TANK FOR INTRODUCING LIQUID DROP THEREINTO AND ANALYZING DEVICE

TECHNICAL FIELD

The present invention relates to a liquid droplet introducing tank and an analyzing device using the same.

BACKGROUND ART

Analyzing specific components of blood is effective for determining the state of health of a human body or treating a specific disease. Examples of blood analyzers used for such applications are blood cell counters that count blood cells such as erythrocytes or leukocytes in blood.

FIG. 26 shows an example of an analyzing device installed in a conventional blood cell counter. The analyzing device X shown in the drawing is provided with a body 91, a diluent tank 92, an introduction portion 93, a dilution tank 94, a recovery tank 95, a weighing tank 96, and an aspiration port 98. When blood 99 is introduced into an introduction port 93a, the blood 99 permeates into flow paths 93c and 93d by capillary phenomenon. When a rotating member 93b is rotated by 90° while in this state, the portion of the blood 99 contained in the flow path 93d is separated. Next, when aspirated from the aspiration port 98, a diluent 92a in the diluent tank 92 and the blood 99 in the flow path 93d are sent to the dilution tank 94. The diluent 92a and the blood 99 are mixed during the course of being sent to the dilution tank 94. As a result, diluted blood is formed in the dilution tank 94.

A partition wall 97 with tiny holes or pores formed therein is provided between the dilution tank 94 and the recovery tank 95. As aspiration from the aspiration port 98 continues, the diluted blood within the dilution tank 94 flows into the recovery tank 95 through the micropore. Electrodes 94a and 95a are provided in the dilution tank 94 and the recovery tank 95. Resistance between the electrodes 94a and 95a is monitored as the diluted blood passes through the micropore. Since erythrocytes, for example, are insulators, resistance decreases each time an erythrocyte passes through the micropore. The total number of erythrocytes contained in the diluted blood can be determined by counting the number of times resistance decreases. The diluted blood that has flowed into the recovery tank 95 is further sent to the weighing tank 96. Flow rate detection means (not shown) comprised of electrical or optical means is provided in front of or in back of the weighing tank 96 in the direction of flow. The amount of diluted blood that has been measured can be obtained by this flow rate detection means. The total number of erythrocytes in the blood 99 is thus counted by using this procedure. The analyzing device X has a comparatively simple structure, and is composed as a so-called disposable type of analyzing device that is used only once and then disposed of.

However, the analyzing device X is required to contain the diluent 92a in a state suitable for analysis. For example, if a minute gap forms in the analyzing device X, there is the risk of leakage of the diluent 92a. In addition, in the case of employing a configuration in which the diluent 92a is sealed in the diluent tank 92, it is necessary to provide means for suitably pumping the diluent 92a by releasing the sealed state when using the analyzing device X. In this manner, it is not easy to suitably contain the diluent 92a in the analyzing device X.

Patent Document 1: WO 03/104771

DISCLOSURE OF THE INVENTION

Problems to be Solved by the Invention

With the foregoing in view, an object of the present invention is to provide a liquid droplet introducing tank and an analyzing device, which have a compact size and enable liquid droplets to be suitably injected therein.

Means for Solving the Problems

According to a first aspect of the present invention, there is provided a liquid droplet introducing tank provided with: a tank body that is formed by a pair of mutually opposing surfaces, and a side surface that spreads out in a direction in which the pair of surfaces are spaced apart; and an injection hole that is opened in one of the pair of surfaces, where liquid droplets are injected from the injection hole, and the center of the injection hole is closer to the side surface than the center of the surface of the pair of surfaces that has the opening.

In a preferable embodiment of the present invention, a portion of an inner surface of the injection hole and a portion of the side surface are flush with each other.

In a preferable embodiment of the present invention, a hydrophilic region that demonstrates hydrophilicity greater than that of other portions is formed on at least one of the pair of surfaces and the side surface.

In a preferable embodiment of the present invention, at least a portion of the hydrophilic region is provided at a location that does not overlap with the opening when viewed in the direction in which the pair of surfaces are spaced apart.

In a preferable embodiment of the present invention, the hydrophilic region is formed by applying at least a drying reagent or a liquid to at least one of the pair of surfaces and the side surface.

In a preferable embodiment of the present invention, at least one of the pair of surfaces is formed with a resistance boundary line that generates a resistance force against the progression of liquid droplets beyond the resistance boundary line, and that extends from a location that overlaps with the opening to a location that does not overlap with the opening when viewed in the direction in which the pair of surfaces are spaced apart.

In a preferable embodiment of the present invention, at least a portion of the side surface is not perpendicular to at least one of the pair of surfaces.

In a preferable embodiment of the present invention, the pair of surfaces are not parallel to each other.

In a preferable embodiment of the present invention, the surface of the pair of surfaces that has the opening is further formed with a rib that surrounds at least a portion of the opening and protrudes toward the surface of the pair of surfaces that does not have the opening.

In a preferable embodiment of the present invention, the surface of the pair of surfaces that has the opening is provided with a swelling member that surrounds at least a portion of the opening and swells by absorbing a portion of the liquid droplets.

In a preferable embodiment of the present invention, the surface of the pair of surfaces that has the opening is formed with a hydrophobic region that surrounds at least a portion of the opening.

According to a second aspect of the present invention, there is provided an analyzing device provided with a liquid droplet introducing tank according to the first aspect of the present invention. The analyzing device is configured to be installed in an analyzer that analyzes specimens containing the liquid droplets injected from the liquid droplet introducing tank.

Other characteristics and advantages of the present invention will be made clearer from the following detailed explanation while referring to the attached drawings.

BEST MODE FOR CARRYING OUT THE INVENTION

The following provides a detailed explanation of preferred embodiments of the present invention with reference to the drawings.

Figure 1:
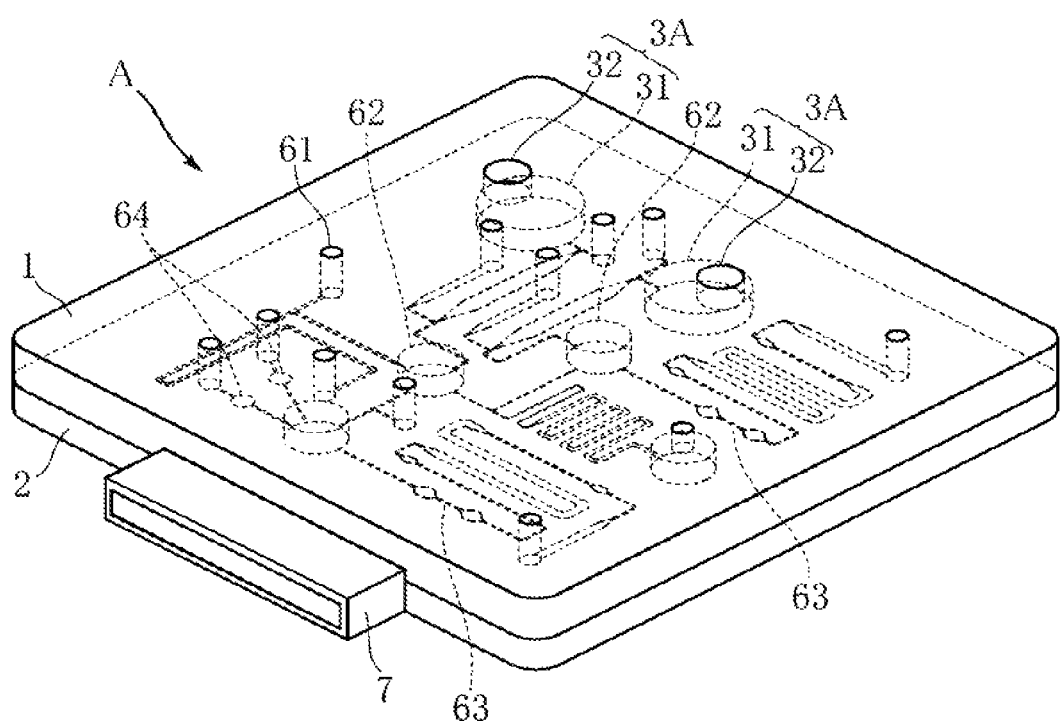
FIG. 1 is a perspective view showing an example of an analyzing device relating to the present invention.

FIG. 1 shows an example of an analyzing device relating to the present invention. An analyzing device A of the present embodiment is composed to be able to be installed in an analyzer (not shown) that carries out cell counting or optical analyses, and is a so-called disposable type of analyzing device for the analyzer. The analyzing device A is composed by laminating a transparent plate 1 and a bottom plate 2, and is provided with a liquid droplet introducing tank 3A, which is a liquid droplet introducing tank based on a first embodiment of the present invention, a blood introduction portion 61, a dilution tank 62, a blood cell counting portion 63, an optical analysis portion 64 and a connector 7.

The transparent plate 1 is a rectangular-shaped plate that is composed of a transparent resin such as acrylic or polyethylene. A plurality of indentations or grooves for forming flow paths or reservoirs to be described later are formed in the transparent plate 1. The bottom plate 2 is, for example, a printed wiring board in which a plurality of base materials composed of epoxy resin and the like are laminated and a wiring pattern composed of copper foil and the like is formed between these base materials. The connector 7 is formed in an extending portion of the bottom plate 2. The connector 7 is used to connect the analyzing device A to the analyzer. The transparent plate 1 and the bottom plate 2 are joined using an adhesive, for example, to be liquid-tight. In addition, both the transparent plate 1 and the bottom plate 2 have hydrophobic surfaces that repel water comparatively easily. Furthermore, the bottom plate 2 may be formed with PET, for example, in the case is not necessary to electrical wiring in the bottom plate 2.

The blood introduction portion 61 is for introducing blood to be analyzed into the analyzing device A. This introduction of blood is carried out by, for example, injecting blood sampled from a subject with a dropper and the like. Blood that has been introduced into the introducing portion 61 is pumped into microchannels by differential pressure generated by pressurization means (not shown) such as a pump provided in the analyzer.

The dilution tank 62 provides a location for diluting blood introduced from the blood introduction portion 61 to a concentration suitable for each type of analysis. A prescribed amount of blood is pumped into this diluent tank 62 along with diluent introduced from the liquid droplet introducing tank 3A. Diluted blood for use as a specimen to be analyzed is obtained by mixing and agitating this blood and diluent.

The blood counting portion 63 is composed to be able to carry out cell counting on the diluted blood using, for example, an electrical resistance detection method, and has a micropore (not shown) provided in a microchannel and a pair of electrodes (not shown) on both sides of this micropore. The pair of electrodes is composed of one or a plurality of types of materials selected from the group consisting of, for example, gold, platinum, palladium and carbon, and is formed in the bottom plate 2 by a printing technique.

The optical analysis portion 64 is a site for measuring Hb or CRP, for example, using an optical technique, and has a reflective film (not shown) provided in a flow path portion enlarged into roughly a circular shape. This reflective film is composed of one type or a plurality of types of materials selected from the group consisting of, for example, gold, platinum and palladium, and is collectively formed in the bottom plate 2 with the electrodes using a printing technique. This reflective film is coated with a reagent (not shown). This reagent makes it possible to measure Hb or CRP by an optical technique when mixed with the diluted blood.

Figure 2:
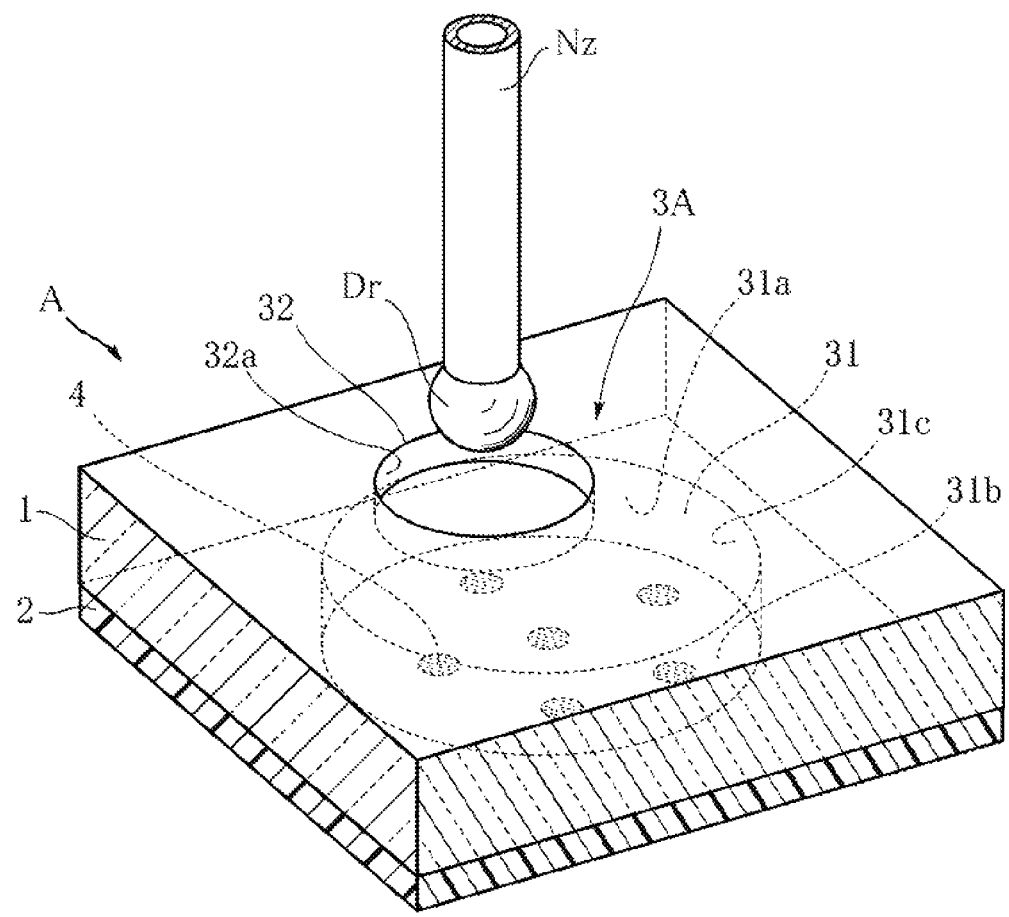
FIG. 2 is a perspective view showing the essential parts of a liquid droplet introducing tank based on a first embodiment of the present invention.

The liquid droplet introducing tank 3A is a site for injecting, for example, pure water for forming diluted blood into the analyzing device A in the form of liquid droplets, and has a tank body 31 and an injection hole 32. As shown in FIG. 2, the tank body 31 is a comparatively shallow tank having a circular cross-section, and is formed by a top surface 31a, a bottom surface 31b and a side surface 31c. The top surface 31a and the side surface 31c constitute the inner surfaces of an indentation having a circular cross-section formed in the transparent plate 1. The bottom surface 31b is a region of the bottom plate 2 that covers the indentation. In the present embodiment, the diameter of the tank body 31 is about 8 mm and the depth is about 2 mm.

Figure 3:
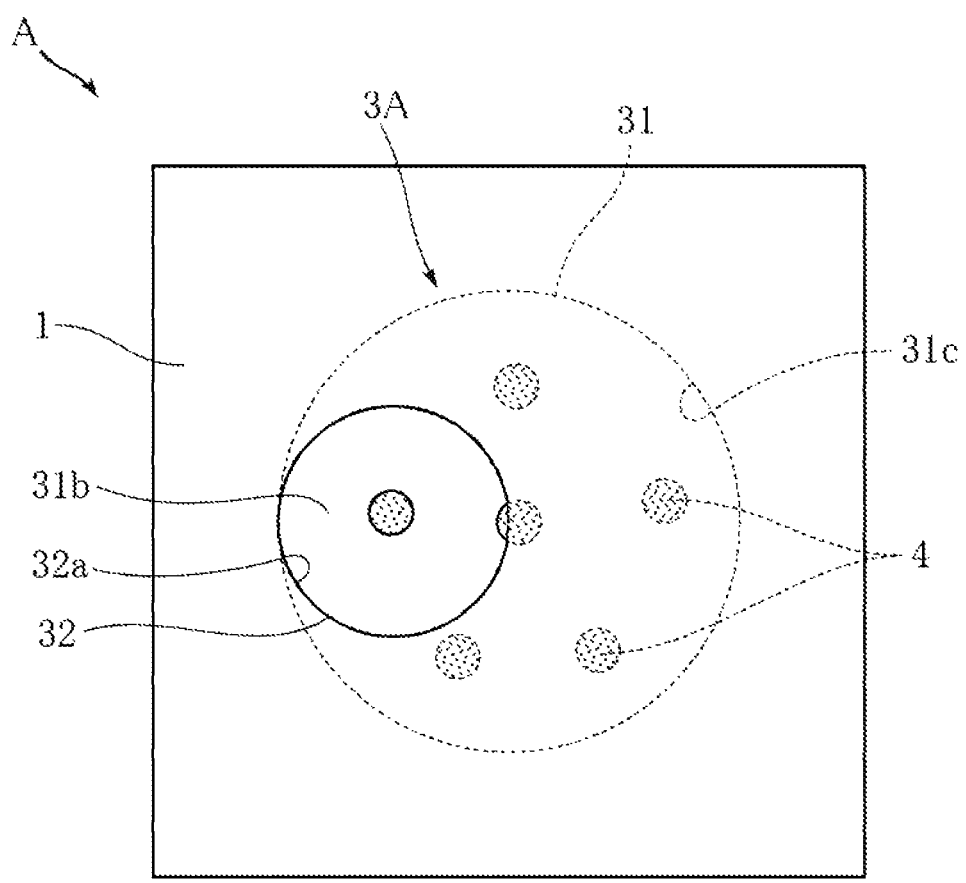
FIG. 3 is an overhead view showing the essential parts of the liquid droplet introducing tank shown in FIG. 2.

The injection hole 32 is a through hole that is opened in the top plate 31a of the tank body 31, and is a site where liquid droplets Dr of pure water pass through from, for example, a nozzle Nz provided in the analyzer. The center of the injection hole 32 is offset from the center of the tank body 31. In the present embodiment, as shown in FIGS. 2 and 3, a portion of an inner surface 32a of the injection hole 32 and a portion of the side surface 31c of the tank body 31 are flush with each other, i.e., arranged within the same plane. The diameter of the injection hole 32 is about 4 mm.

A drying reagent 4 is applied to the inner surface 31b. The drying reagent 4 consists of a mixture of a salt and a polymer compound such as polyvinylpyrrolidone (PVP), and is for forming physiological saline suitable for diluting blood by being dissolved in the injected pure water. The drying reagent 4 is obtained by absorbing liquid droplets Dr and completely dissolving therein, the hydrophilicity thereof with respect to the liquid droplets Dr is considerably higher than the inner surface 31b, and corresponds to an example of a hydrophilic region as referred to in the present invention. In the present embodiment, the drying reagent 4 is coated in the form of six small circles. As is clearly depicted in FIG. 3, one of the small circular portions is coated at a location that completely overlaps with the injection hole 32. The other five small circular portions are coated at locations that are completely or nearly completely hidden from the injection hole 32.

The following provides an explanation of the operation of the analyzing device A and the liquid droplet introducing tank 3A.

Figure 4:
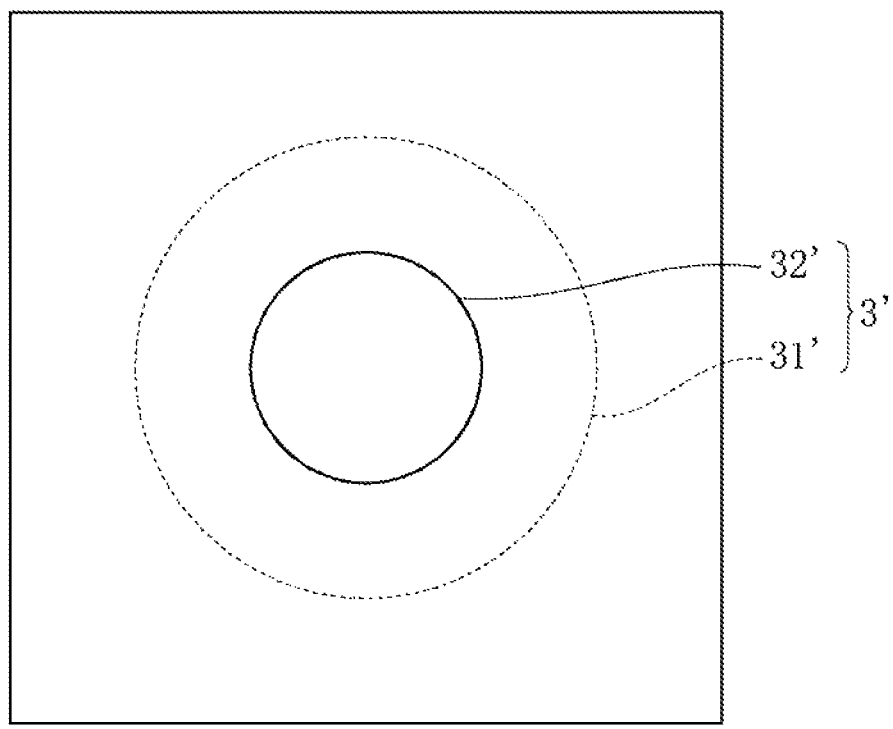
FIG. 4 is an overhead view showing the essential parts of a reference example of a liquid droplet introducing tank.

FIG. 4 shows a reference example for comparing injection of liquid droplets into the liquid droplet introducing tank 3A in the analyzing device A. The liquid droplet introducing tank 3A' of this reference example is provided with a tank body 31' and an injection hole 32' that are similar to the previously described tank body 31 and the injection hole 32. However, the centers of the tank body 31' and the injection hole 32' are arranged to mutually coincide, and this differs from the previously described liquid droplet introducing tank 3A. In addition, differing from the liquid droplet introducing tank 3A, a drying reagent 4 is not coated in the liquid droplet introducing tank 3A'.

Figure 5:
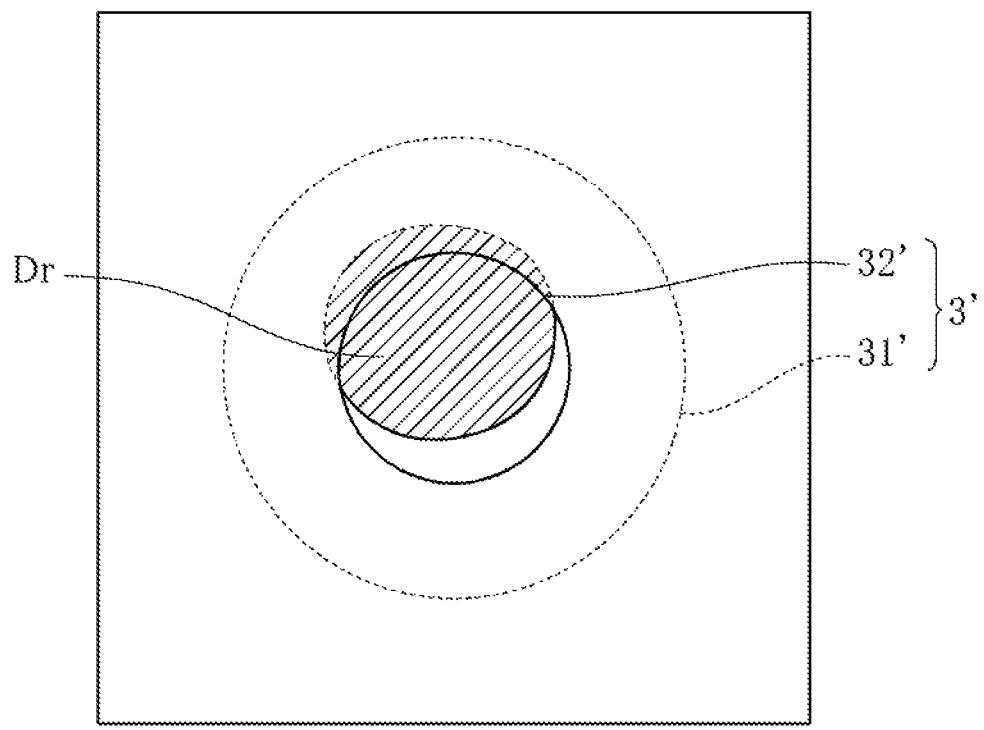
FIG. 5 is an overhead view showing essential parts depicting injection of liquid droplets into the liquid droplet introducing tank of FIG. 4.
Figure 6:
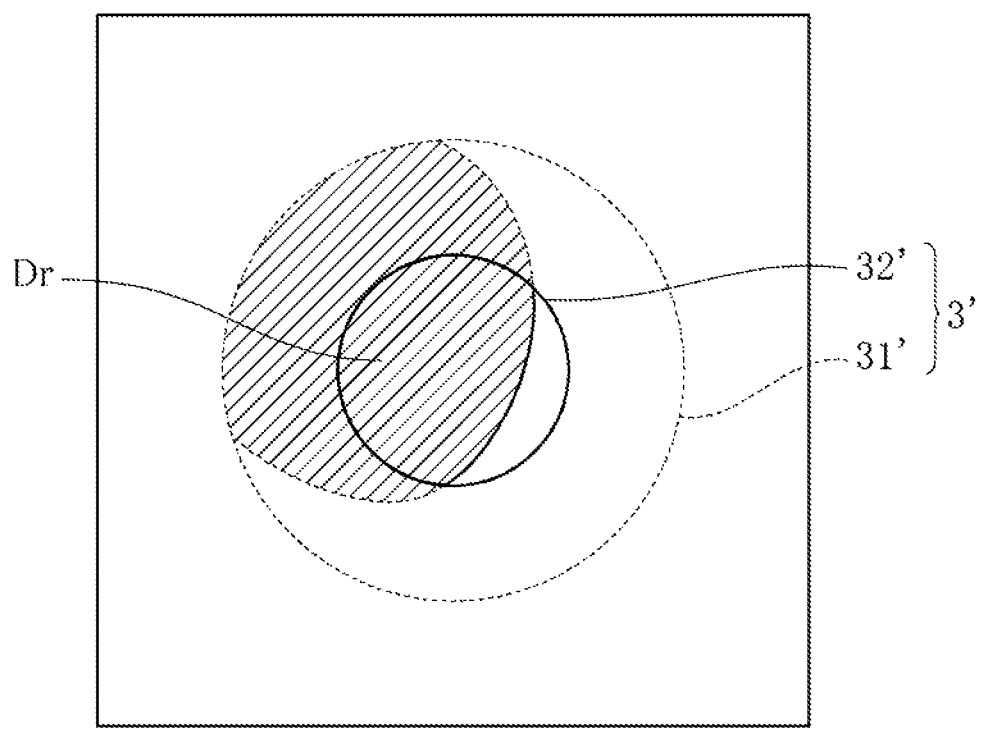
FIG. 6 is an overhead view showing essential parts depicting injection of liquid droplets into the liquid droplet introducing tank shown in FIG. 4.
Figure 7:
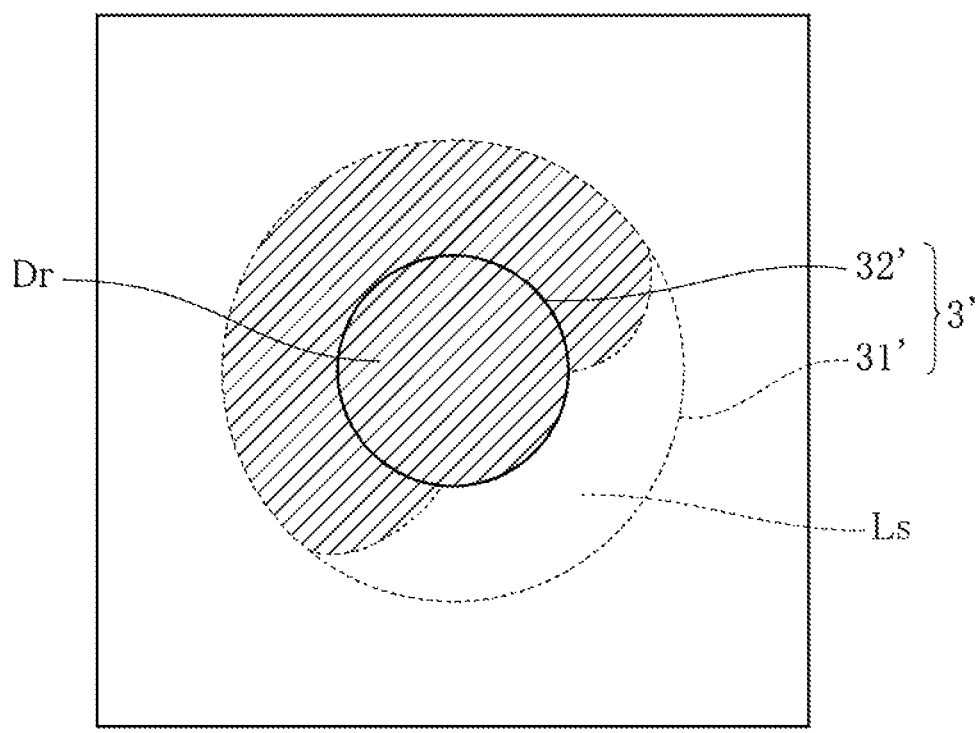
FIG. 7 is an overhead view showing essential parts depicting injection of liquid droplets into the liquid droplet introducing tank shown in FIG. 4.

As shown in FIG. 5, when liquid droplets Dr are injected from the injection hole 32', the liquid droplets Dr accumulate in a portion directly below the injection hole 32 in a state in which they contact the top surface and bottom surface that form the tank body 31'. This is because the liquid droplets Dr are inhibited from spreading out from the injection hole 32' since surface tension acts on the liquid droplets Dr to make the surface area thereof as small as possible. When liquid droplets Dr are further injected, the liquid droplets Dr gradually spread out over the tank body 31'. As shown in FIG. 6, a portion of the liquid droplets Dr reach a side surface of the tank body 31'. When injection is subsequently continued, the contact surface area between the liquid droplets Dr and the side surface increases. However, since surface tension acts on the liquid droplets Dr so as to make the surface area thereof as small as possible, the surface area of the liquid droplets Dr gradually increases without hardly any deviation from the injection hole 32'. When injection of the liquid droplets Dr continues further, the entire injection hole 32' is completely blocked by the liquid droplets Dr as shown in FIG. 7.

It is no longer possible to continue to inject the liquid droplets Dr beyond this point. At this time, space within the tank body 31' that is not filled by the liquid droplets Dr becomes a residual space Ls. In the liquid droplet introducing tank 3A', since the liquid droplets Dr hardly deviate at all from the center of the injection hole 32', namely the center of the tank body 31', the injection hole 32' ends up being blocked by the liquid droplets Dr before the liquid droplets Dr fully spread out in the tank body 31'. Consequently, the residual space Ls easily accounts for a comparatively large proportion of the tank body 31'. As the size of the residual space Ls increases, it becomes necessary to make the volume of the tank body 31' much larger than a desired amount of liquid droplets Dr in order to inject that desired amount. This situation impairs reducing the size of the liquid droplet introducing tank 3A' and in turn, the size of the analyzing device in which it is contained. There is a strong need to reduce the size of disposable type analyzing devices in particular in order to respond to requirements such as ease of use and cost reductions.

In contrast, the following provides an explanation of injecting liquid droplets Dr into the liquid droplet introducing tank 3A of the analyzing device A of the present embodiment with reference to FIGS. 8 to 11.

Figure 8:
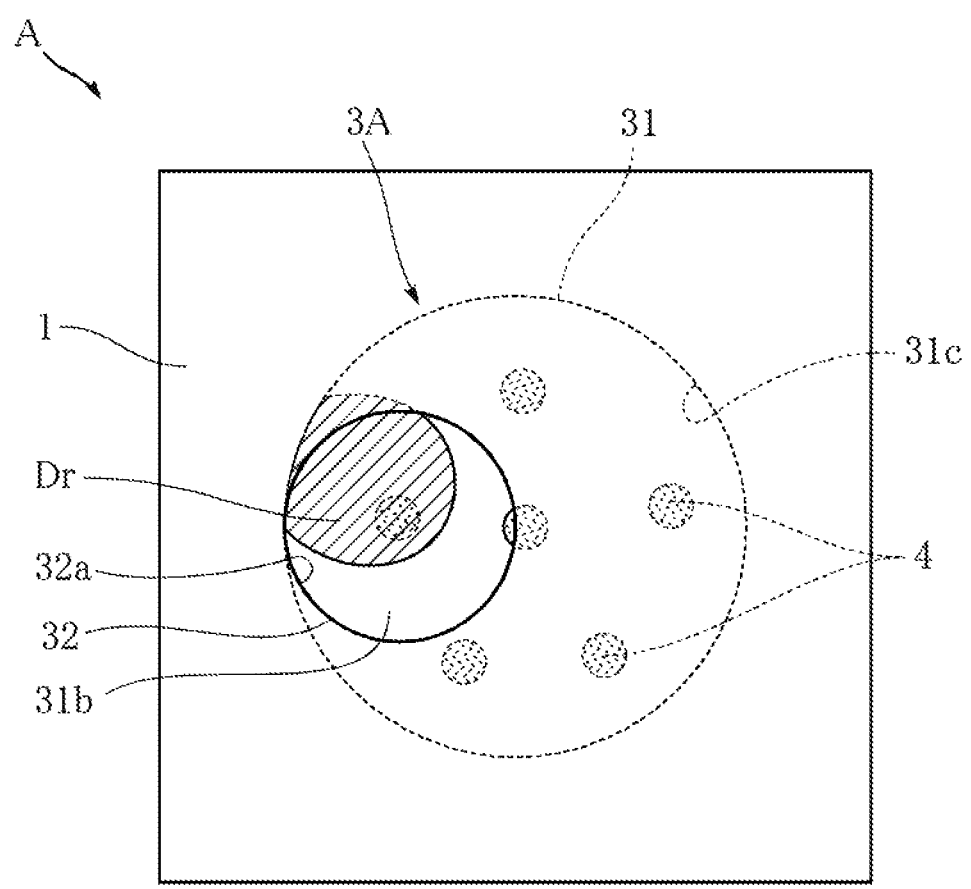
FIG. 8 is an overhead view showing essential parts depicting injection of liquid droplets into the liquid droplet introducing tank of the analyzing device shown in FIG. 1.
Figure 9:
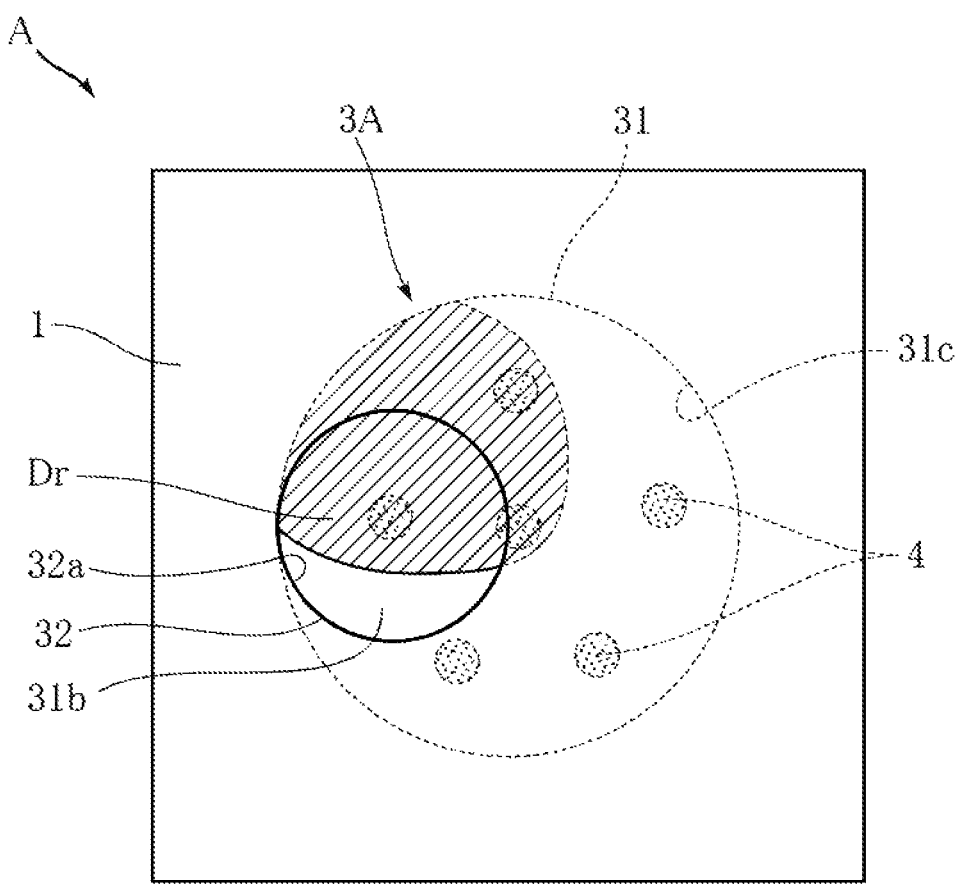
FIG. 9 is an overhead view showing essential parts depicting injection of liquid droplets into the liquid droplet introducing tank shown in FIG. 2.
Figure 10:
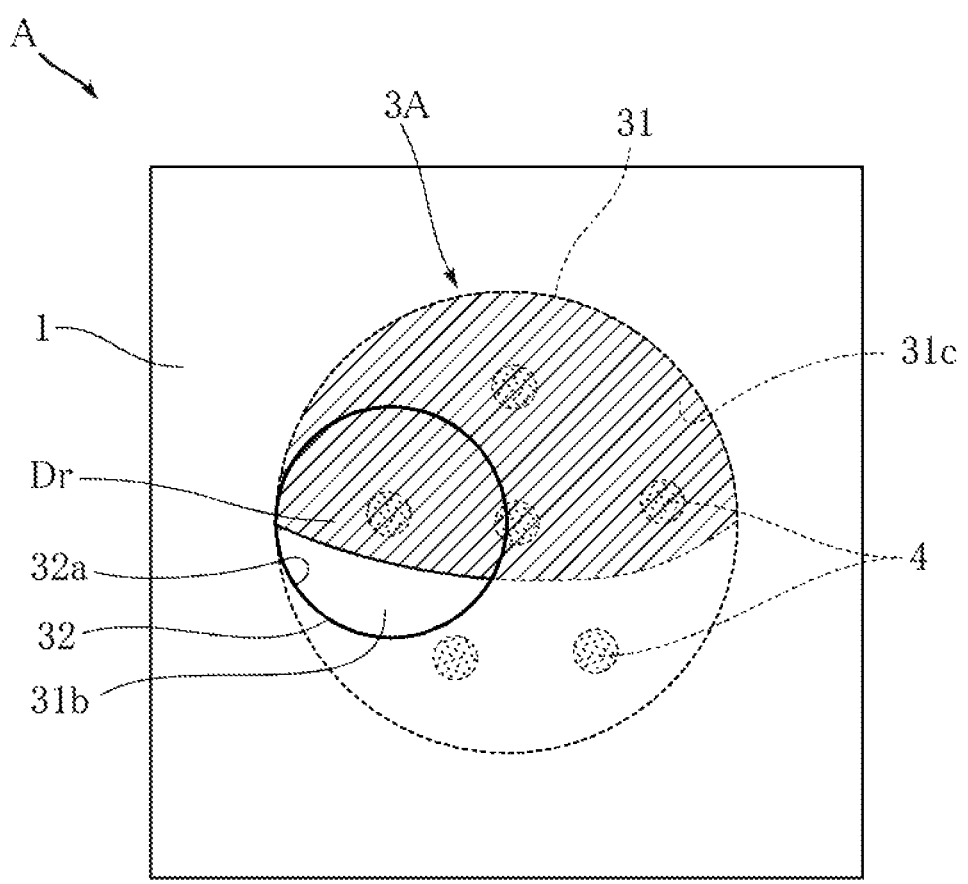
FIG. 10 an overhead view showing essential parts depicting injection of liquid droplets into the liquid droplet introducing tank shown in FIG. 2.

First, as shown in FIG. 8, liquid droplets Dr are injected from the injection hole 32. Since the injection hole 32 is located off-center from the tank body 31 to a degree such that a portion of the inner surface 32a thereof and a portion of the side surface 31c are arranged within the same plane, the liquid droplets Dr rapidly contact the side surface 31c. As injection of the liquid droplets Dr continues, the liquid droplets Dr spread out so as to follow the side surface 31c as shown in FIG. 9. In addition, wetting force generated at those portions of the liquid droplets Dr in contact with the top surface 31a and the bottom surface 31b acts to inhibit the liquid droplets Dr from spreading out. However, when the liquid droplets Dr contact the drying reagent 4, the drying reagent 4 immediately absorbs the liquid droplets Dr. As a result, the liquid droplets Dr spread out so as to be attracted to the drying reagent 4.

As injection of the liquid droplets Dr continues further, spreading along the side surface 31c and spreading through contact with the drying reagent 4 occur alternately or simultaneously. As a result of the liquid droplets Dr being actively forced to spread out, accumulation of the liquid droplets Dr in the vicinity of the injection hole 32 can be prevented. As a result, complete blockage of the injection hole 32 by the liquid droplets Dr can be avoided.

Figure 11:
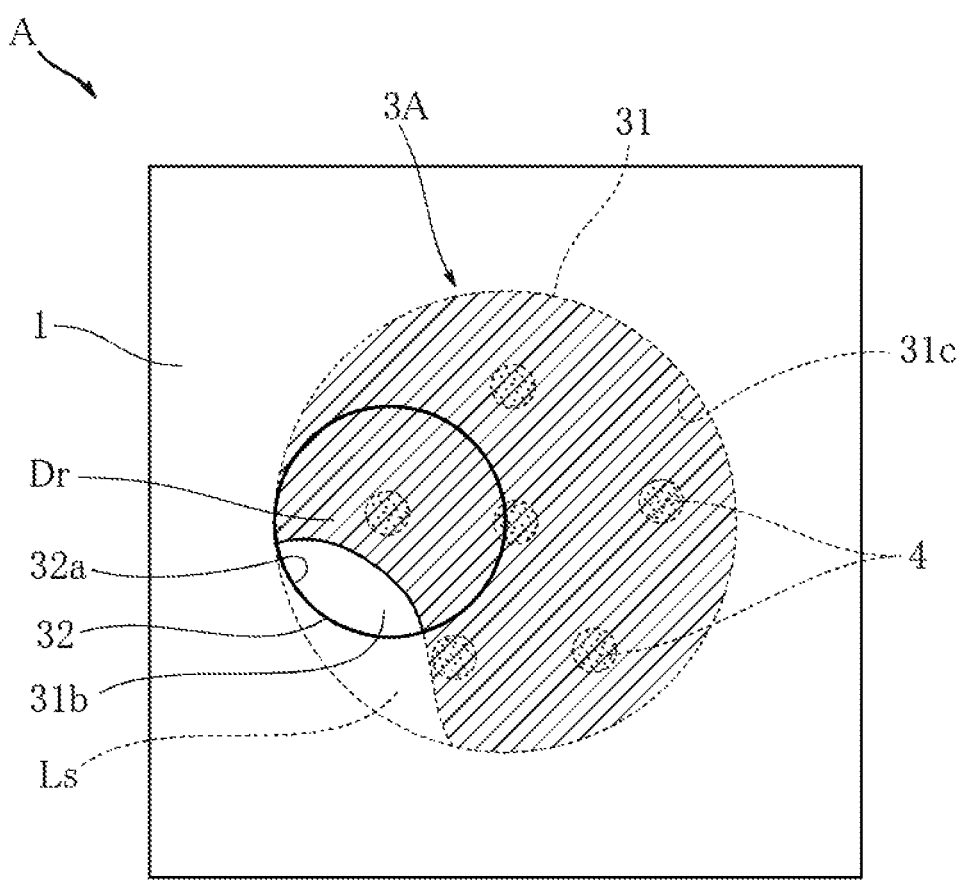
FIG. 11 is an overhead view showing essential parts depicting injection of liquid droplets into the liquid droplet introducing tank shown in FIG. 2.

As injection of the liquid droplets Dr continues further, the state shown in FIG. 11 is reached. When in this state, the liquid droplets Dr spread out to a degree that they contact all of the drying reagents 4. In addition, the majority of the side surface 31c is wetted by the liquid droplets Dr. As a result, the residual space Ls of the tank body 31 can be made to be quite small as compared with, for example, the residual space Ls in the reference example shown FIG. 7. This is advantageous for reducing the size of the tank body 31 and in turn, the analyzing device A, and is suitable for using the analyzing device A as a disposable type of analyzing device.

FIGS. 12 to 23 indicate other embodiments of the present invention. Furthermore, the same reference symbols as those used in the present embodiment are used in these drawings to indicate those constituent features that are identical or similar to the constituent features of the above-mentioned embodiment.

Figure 12:
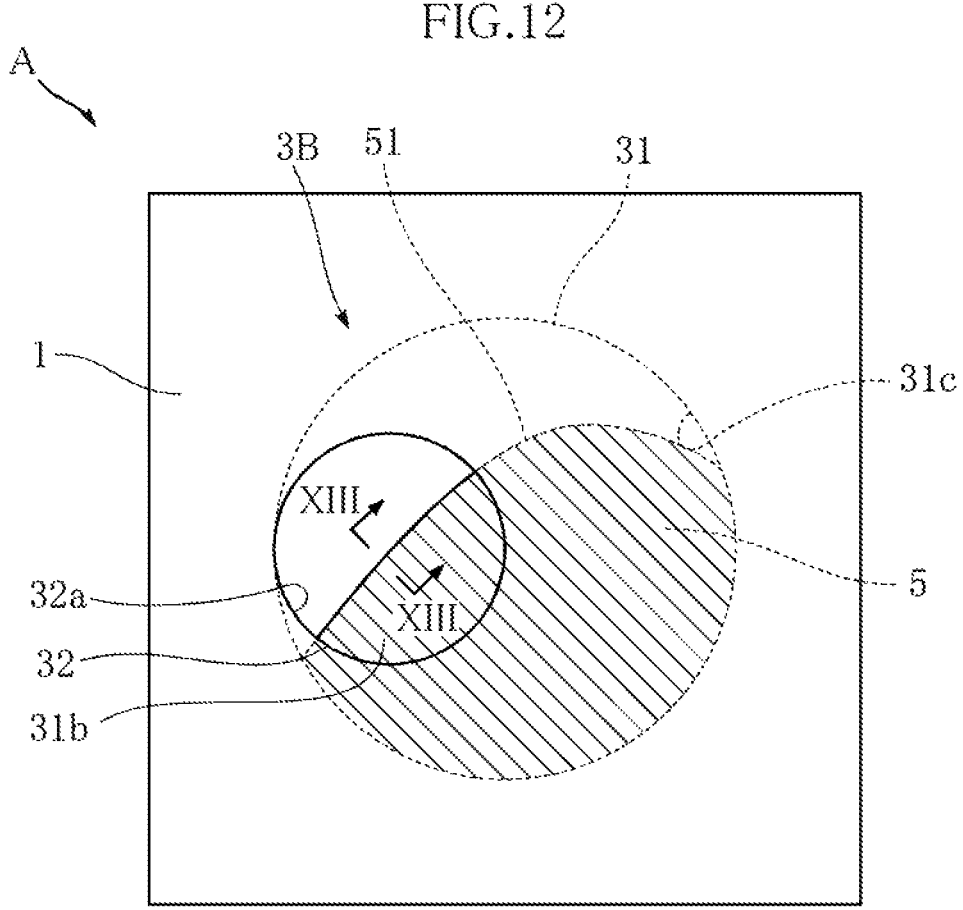
FIG. 12 is an overhead view showing the essential parts of a liquid droplet injection bank based on a second embodiment of the present invention.
Figure 13:
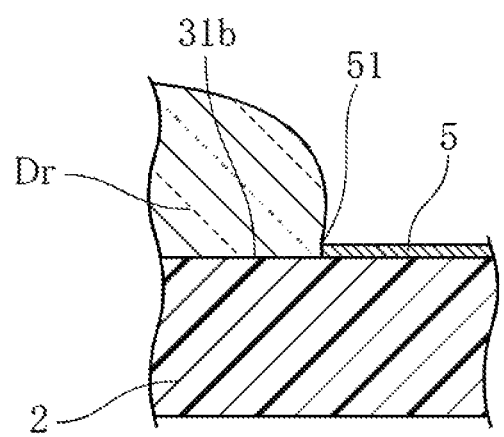
FIG. 13 is a cross-sectional view showing essential parts taken along line XIII-XIII of FIG. 12.

FIGS. 12 and 13 show a liquid droplet introducing tank based on a second embodiment of the present invention. A liquid droplet introducing tank 3B of the present embodiment differs from the previously described embodiment in that a metal film 5 is formed on the bottom surface 31b instead of the previously described drying reagent 4. The metal film 5 is composed of one type or a plurality of types of materials selected from the group consisting of, for example, gold, platinum, palladium and carbon, and is formed on the bottom plate 2 by a printing technique. This metal film 5 can be collectively formed with electrodes of the above-mentioned blood cell counting portion 63 or a reflecting portion of the optical analysis portion 64. As is clearly depicted in FIG. 12, the metal film 5 covers a region that is roughly more than half of the bottom surface 31b. The edge of the metal film 5 forms a resistance boundary line 51.

As shown in FIG. 13, the resistance boundary line 51 constitutes a minute level difference formed on the bottom surface 31b. This resistance boundary line 51 demonstrates a resistance force that inhibits spreading of the liquid droplets Dr when the liquid droplets Dr attempt to spread out from the bottom surface 31b to the metal film 5. Since the liquid droplets Dr do not easily go beyond the resistance boundary line 51, during initial injection of the liquid droplets Dr, the liquid droplets Dr rapidly contact the side surface 31c and spread out along the side surface 31c over a region not covered by the metal film 5. Since the resistance boundary line 51 extends from a region overlapping with the injection hole 32 to a region not overlapping with the injection hole 32, the liquid droplets Dr do not accumulate at the injection hole 32, but rather spread out from the injection hole 32 to a region not overlapping with the injection hole 32. When nearly the entire region not covered by the metal film 5 is filled by the liquid droplets Dr, the liquid droplets Dr spread out over the metal film 5 in opposition to the resistance force generated by the resistance boundary line 51. This spreading occurs along the side surface 31c. The formation of a gradually curved shape along the side surface 31c by the portion of the resistance boundary line 51 in the vicinity of the right side of the drawing is suitable for causing the liquid droplets Dr to spread out along the side surface 31c.

Instead of forming the metal film 5, an adhesive layer for adhering the transparent plate 1 and the bottom plate 2, for example, may be formed in the same region as the metal film 5 as means for forming the resistance boundary line 51. The adhesive used for such applications is made of resin that demonstrates strong hydrophobicity in the majority of cases. Moreover, similar to the case of providing the metal film 5, the resistance boundary line 51 has a level difference that corresponds to the thickness of the adhesive. Liquid droplets Dr can be suitably injected in the case of providing this type of resistance boundary line 51 as well.

Figure 14:
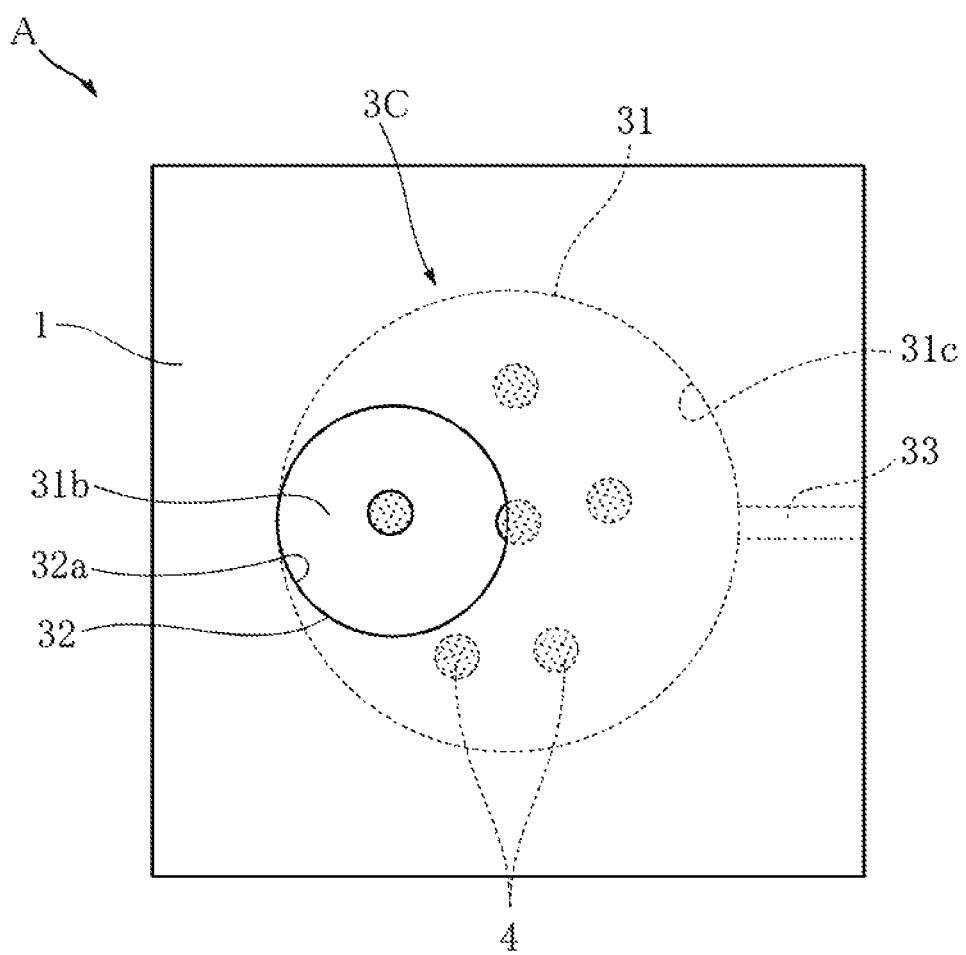
FIG. 14 is an overhead view showing the essential parts of a liquid droplet introducing tank based on a third embodiment of the present invention.
Figure 15:
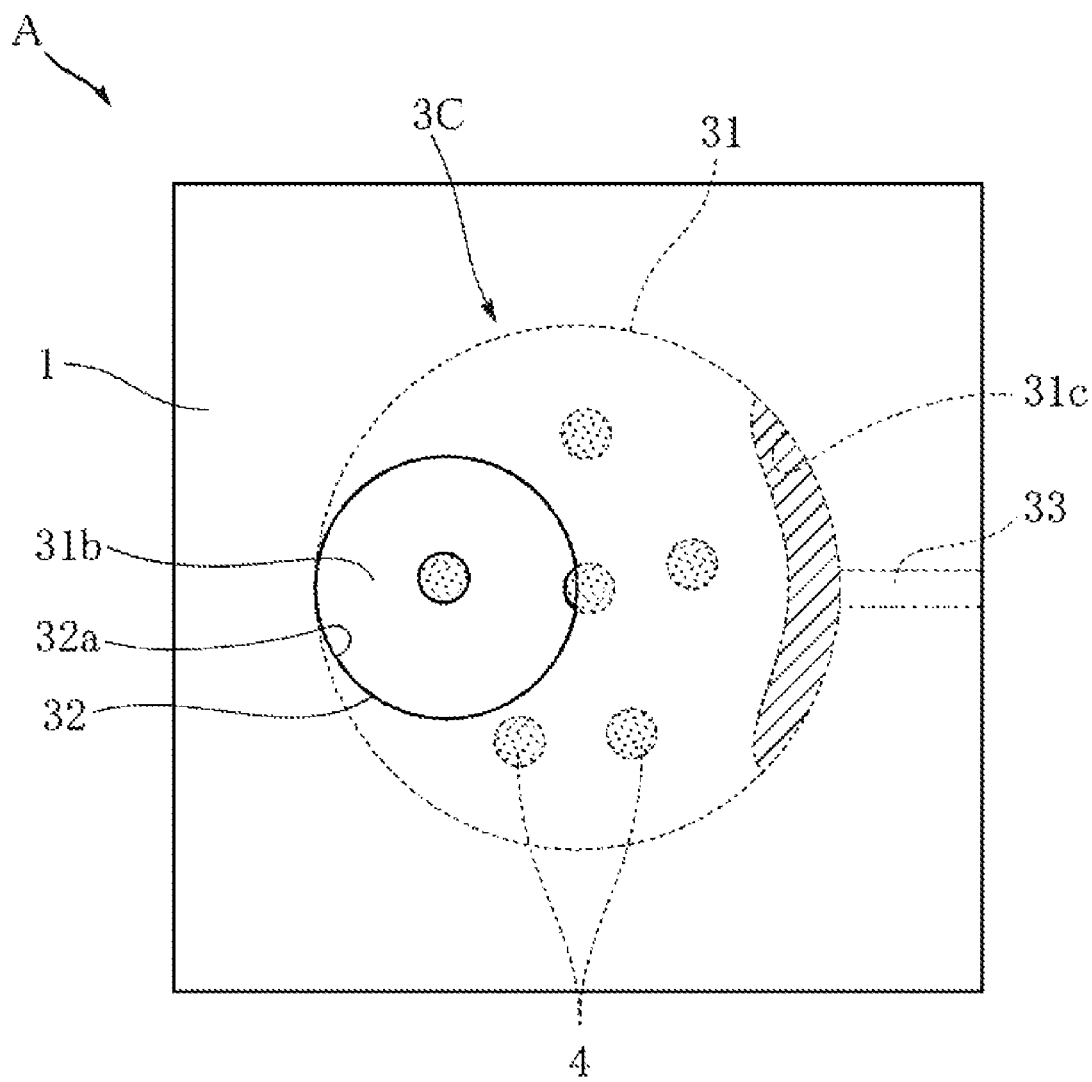
FIG. 15 is an overhead view showing essential parts of a state in which liquid droplets are supplied to the liquid droplet introducing tank shown in FIG. 14.

FIG. 14 shows a liquid droplet introducing tank based on a third embodiment of the present invention. In a liquid droplet introducing tank 3C of the present embodiment, means for providing a hydrophilic region differs from the previously described embodiments. A liquid supply hole 33 is provided in the liquid droplet introducing tank 3C. The liquid supply hole 33 is a hole having a comparatively small cross-section that is opened in the side surface 31c. A liquid supply source not shown is connected to the liquid supply hole 33. As shown in FIG. 15, a liquid is supplied from the liquid supply source to the tank body 31 through the liquid supply hole 33 either simultaneously to or before or after the start of injection of liquid droplets Dr from the injection hole 32. The amount of the liquid is an amount to a degree that those portions of the top surface 31a, the bottom surface 31b and the side surface 31c in the vicinity of the liquid supply hole 33 become wet. As a result, those regions of the top surface 31a, the bottom surface 31b and the side surface 31c that are wetted by the liquid constitute a hydrophilic region. This hydrophilic region promotes spreading of the liquid droplets Dr that have been injected from the injection hole 32, and is suitable for enabling the liquid droplets Dr to spread out evenly within the tank body 31.

Figure 16:
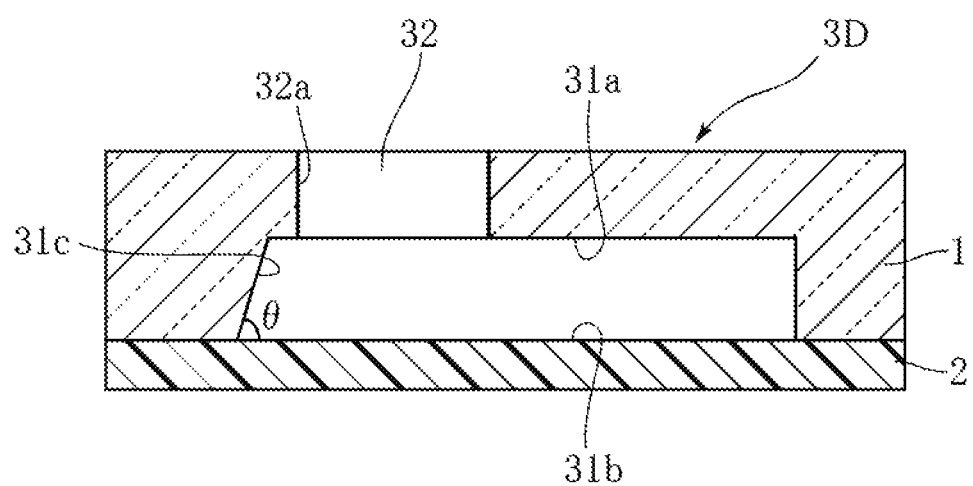
FIG. 16 is an overhead view showing the essential parts of a liquid droplet introducing tank based on a fourth embodiment of the present invention.

FIG. 16 shows a liquid droplet introducing tank based on a fourth embodiment of the present invention. A liquid droplet introducing tank 3D of the present embodiment differs from the previously described embodiments in that a portion of the side surface 31c is non-parallel to the top surface 31a and the bottom surface 31b. The portion of the side surface 31c of the present embodiment in the vicinity of the injection hole 32 is inclined, and more specifically, an angle θ formed by the side surface 31c and the bottom surface 31b is an acute angle. According to this embodiment, contact surface area between liquid droplets Dr injected from the injection hole 32 and the bottom surface 31b and the side surface 31c increases by the amount of inclination of the side surface 31c. As a result, a stronger wetting force acts on the liquid droplets Dr, thereby making it possible to expect the effect of the liquid droplets Dr more readily spreading out along the side surface 31c. Furthermore, although the liquid droplets Dr easily spread out along the side surface 31c if the angle θ is an acute angle, the present invention is not limited thereto, but rather the angle θ is only required to be set so that the wetting force acting on the liquid droplets Dr acts advantageously for allowing the liquid droplets Dr to spread out.

Figure 17:
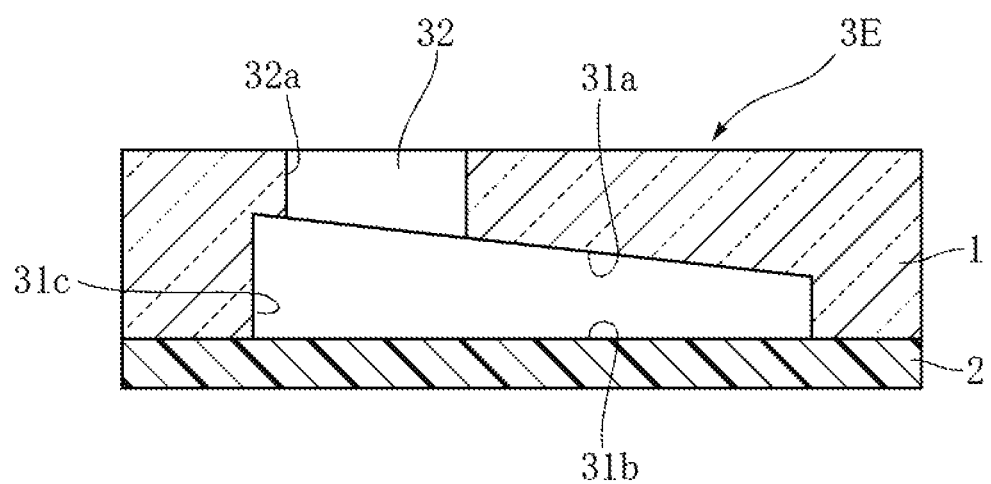
FIG. 17 is an overhead view showing the essential parts of a liquid droplet introducing tank based on a fifth embodiment of the present invention.

FIG. 17 shows a liquid droplet introducing tank based on a fifth embodiment of the present invention. A liquid droplet introducing tank 3E of the present invention differs from the previously described embodiments in that the top surface 31a and the bottom surface 31b are not parallel. More specifically, the top surface 31a is inclined slightly relative to the horizontally level bottom surface 31b. Moreover, the top surface 31a is inclined in the radial direction of the tank body 31 from the location where the injection hole 32 opens towards the bottom surface 31b moving towards the opposite side from the injection hole 32. According to this embodiment, liquid droplets Dr that have been injected from the injection hole 32 easily spread out towards portions farther away from the injection hole 32. This is because the contact surface area increases the closer the top surface 31a is to the bottom surface 31b even for liquid droplets Dr of the same volume, and this results in a corresponding increase in wetting force.

Figure 18:
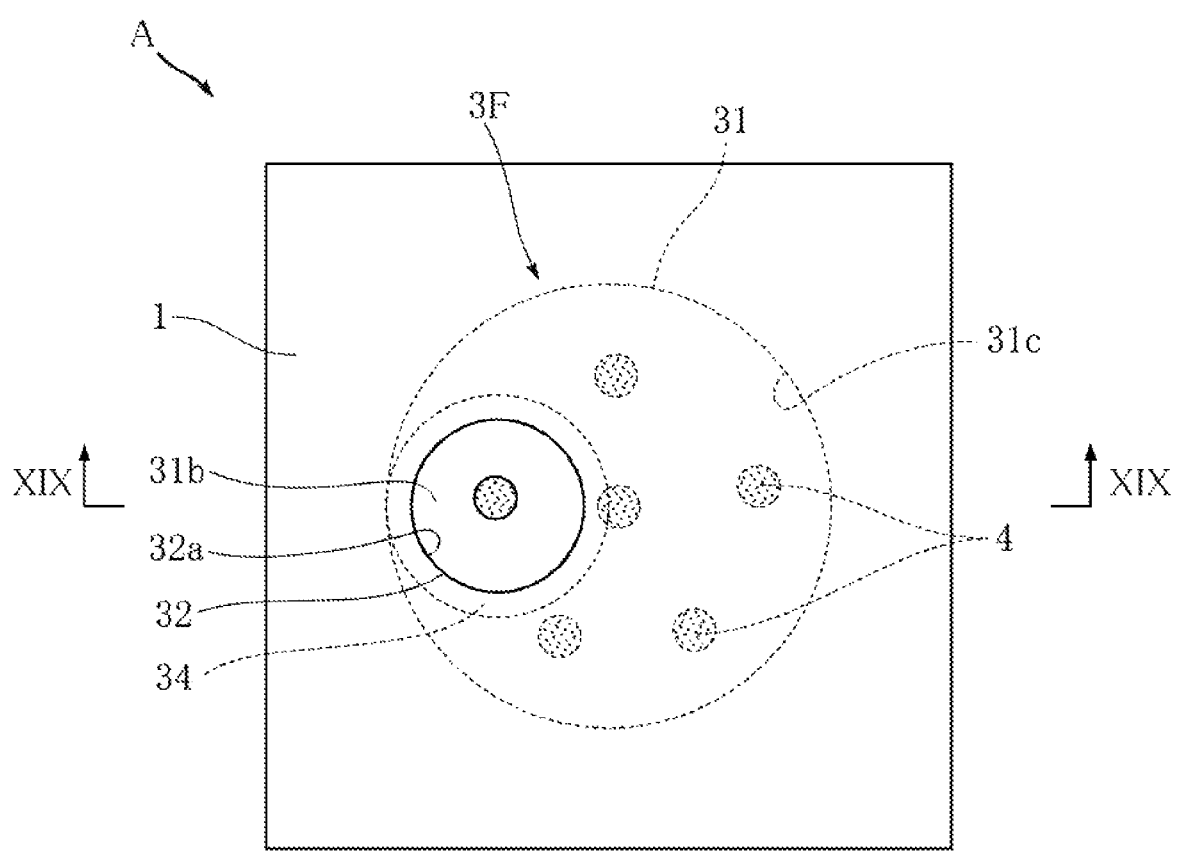
FIG. 18 is an overhead view showing the essential parts of a liquid droplet introducing tank based on a sixth embodiment of the present invention.
Figure 19:
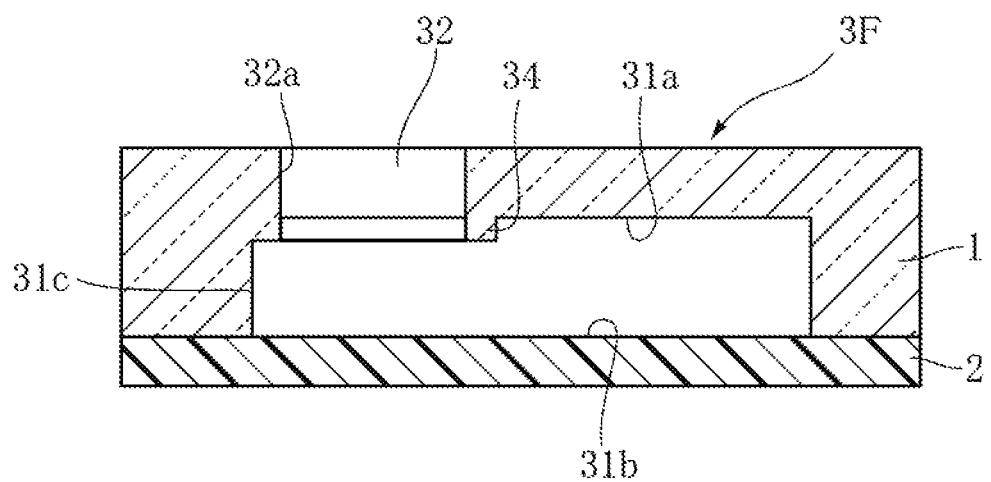
FIG. 19 is a cross-sectional view showing essential parts taken along line XIX-XIX of FIG. 18.

FIGS. 18 and 19 show a liquid droplet introducing tank based on a sixth embodiment of the present invention. A liquid droplet introducing tank 3F of the present embodiment differs from the previously described embodiments in that it has a rib 34. The rib 34 surrounds the opening 32 and protrudes from the top surface 31a towards the bottom surface 31b.

Figure 20:
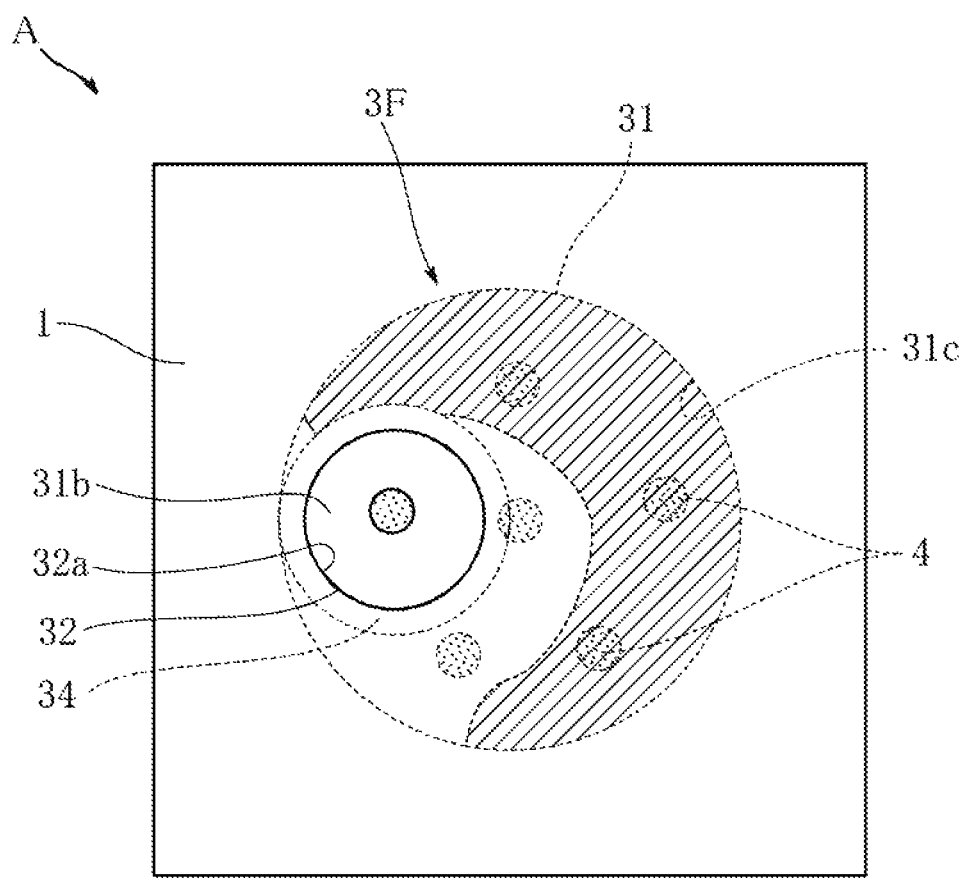
FIG. 20 is an overhead view showing essential parts depicting liquid droplets flowing into the liquid droplet introducing tank of FIG. 18.
Figure 21:
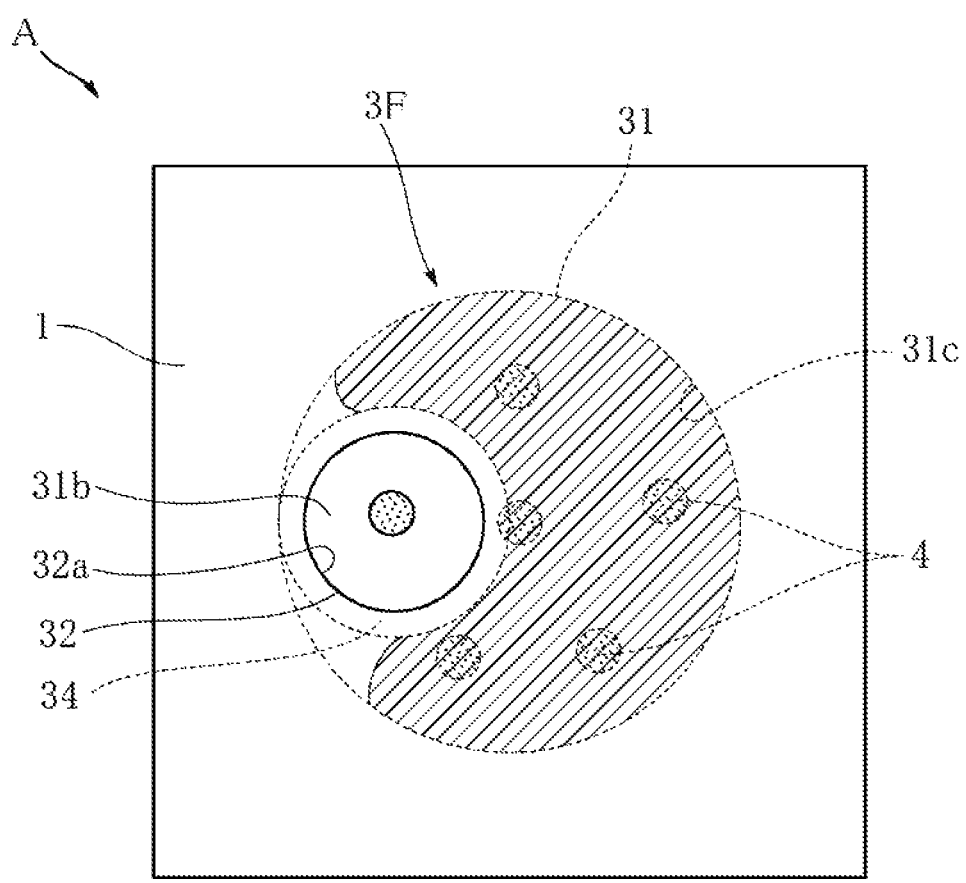
FIG. 21 is an overhead view showing essential parts depicting liquid droplets flowing into the liquid droplet introducing tank of FIG. 18.
Figure 22:
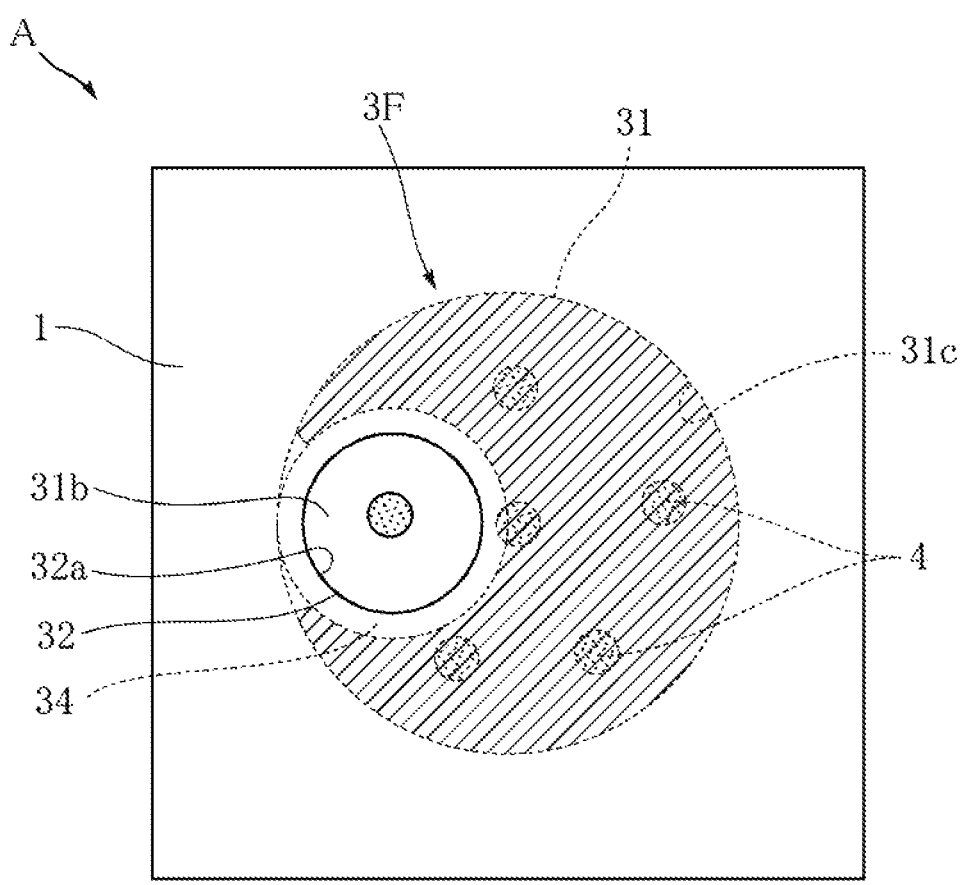
FIG. 22 is an overhead view showing essential parts depicting liquid droplets flowing into the liquid droplet introducing tank of FIG. 18.
Figure 23:
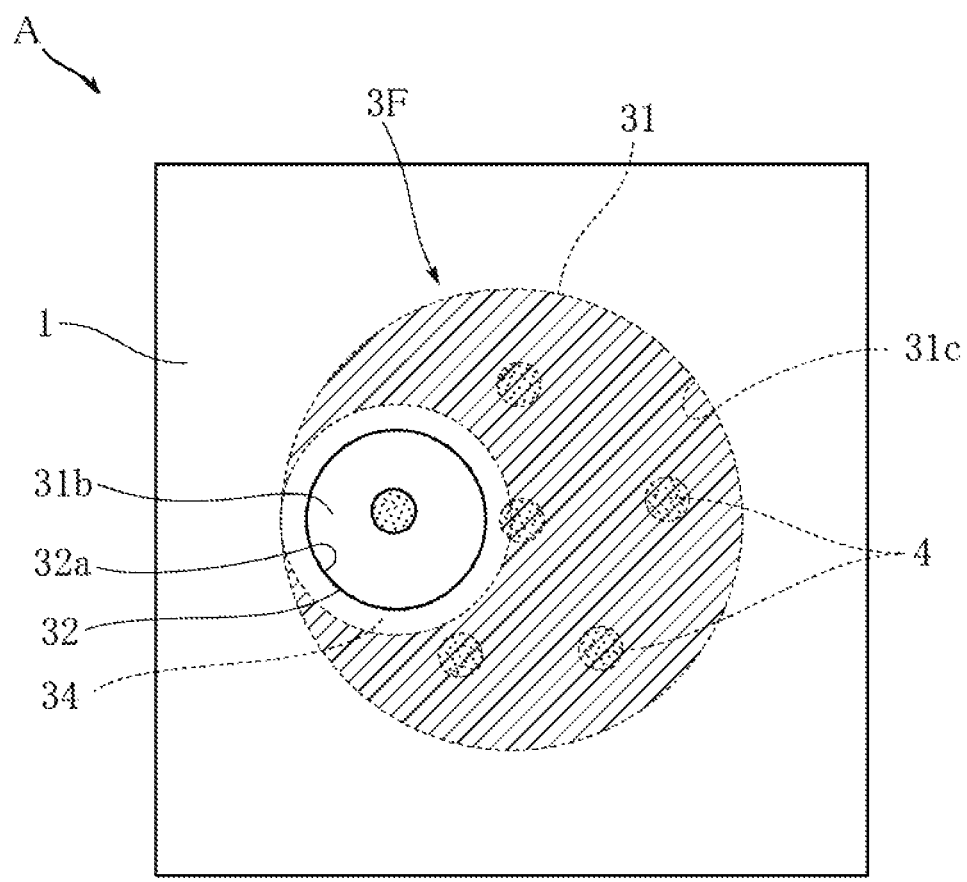
FIG. 23 is an overhead view showing essential parts depicting liquid droplets flowing into the liquid droplet introducing tank of FIG. 18.

When liquid droplets Dr are injected into this liquid droplet introducing tank 3F, the liquid droplets Dr spread out between the side surface 31c and the rib 34 as shown in FIG. 20. This is because the level difference formed by the rib 34 functions as a barrier that inhibits the droplets Dr from flowing into the injection hole 32. Consequently, as injection of the liquid droplets Dr continues, the liquid droplets Dr selectively spread out over the region between the side surface 31c and the rib 34 as shown in FIGS. 21 and 22. During the course of this spreading, air that was present within the tank body 31 is rapidly evacuated from the injection hole 32. The entire region between the side surface 31c and the rib 34 can be then be filled by the liquid droplets Dr as shown in FIG. 23. According to this type of embodiment, the residual space Ls can be nearly completely eliminated. Furthermore, the rib 34 is not limited to a perfect circle, but rather is only required to surround at least a portion of the opening 32. Consequently, the rib 34 may be arranged in the shape of a letter "C" in which a portion of the circle is missing, or may be arranged so that a plurality of small projections surrounds the opening 32 in the form of a ring.

Figure 24:
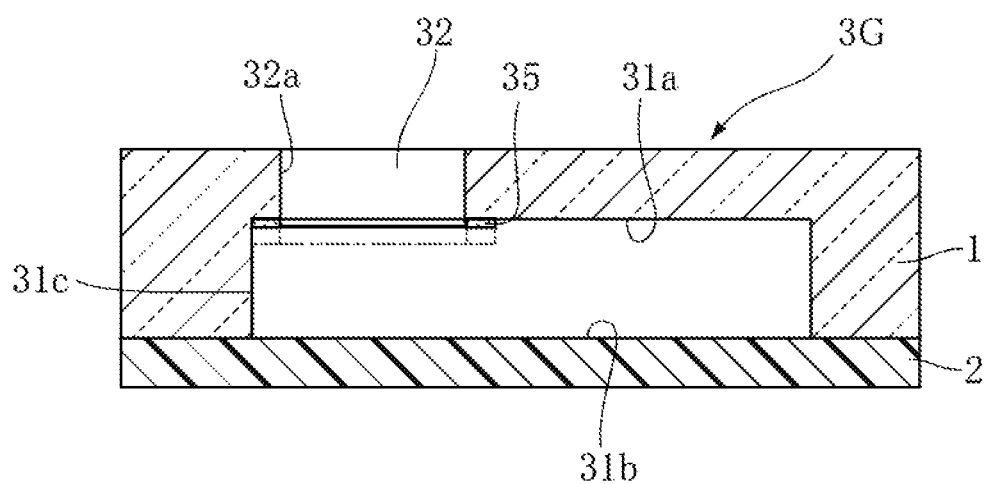
FIG. 24 is a cross-sectional view showing the essential parts of a seventh embodiment of a liquid droplet introducing tank relating to the present invention.

FIG. 24 shows a liquid droplet introducing tank based on a seventh embodiment of the present invention. A liquid droplet introducing tank 3G of the present embodiment differs from the previously described embodiments in that it is provided with a swelling member 35. The swelling member 35 is composed of a material in which the volume thereof swells to several times to several hundred times its initial volume as a result of absorbing a portion of the liquid droplets Dr. Examples of such materials that may be used include Aquacork (Sumitomo Seika Chemicals), Wonder-Gel (Kao), Sanwet (Sanyo Chemical Industries) and Aqua Reserve GP (Nippon Synthetic Chemical Industry). The swelling member 35 is provided on the top surface 31a, and is in the form or a ring that surrounds at least a portion of the opening 32. When liquid droplets Dr are injected into the opening 32, the swelling member 35 swells from the top surface 31a towards the bottom surface 31b as a result of absorbing a portion of the liquid droplets Dr (as indicated with a virtual line in the drawing). This type of configuration also makes it possible to prevent the opening 32 from being blocked by the liquid droplets Dr.

Figure 25:
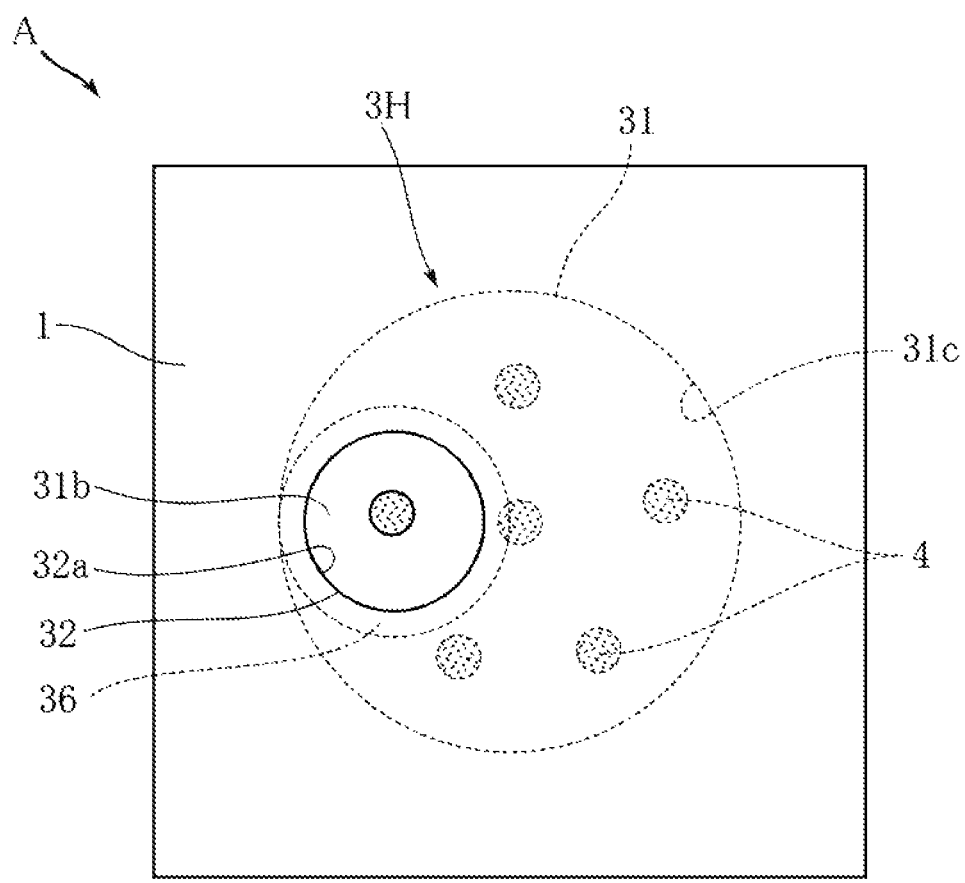
FIG. 25 is a cross-sectional view showing the essential parts of an eighth embodiment of a liquid droplet introducing tank relating to the present invention.
Figure 26:
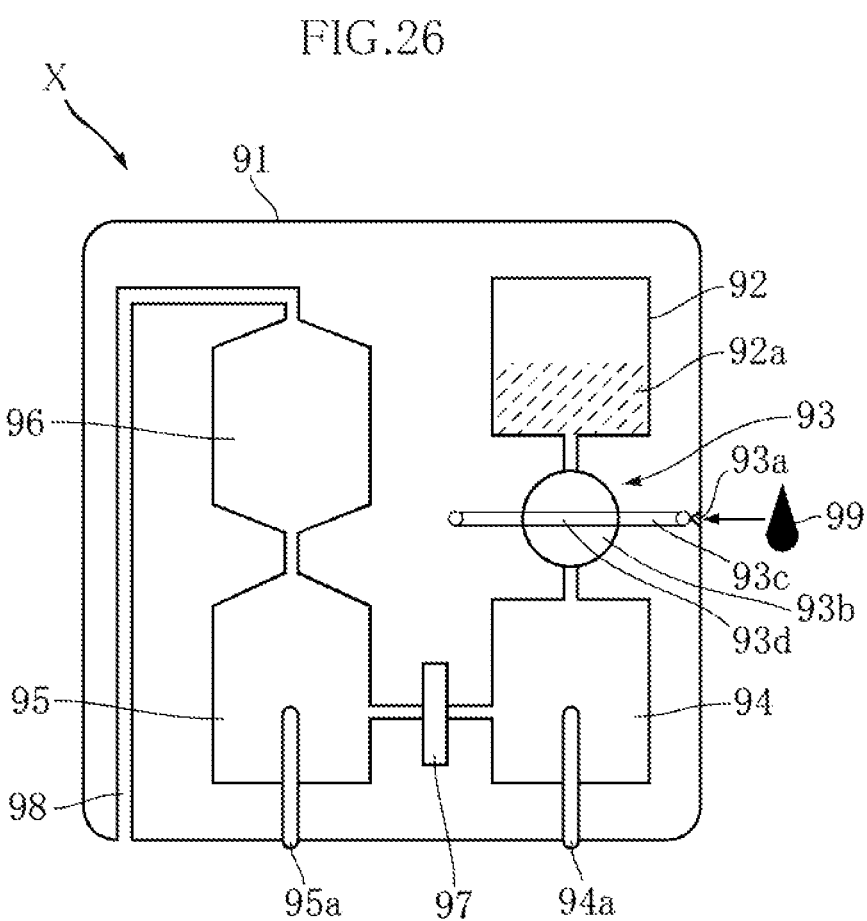
FIG. 26 is an overhead view showing an example of a conventional analyzing device.

FIG. 25 shows a liquid droplet introducing tank based on an eighth embodiment of the present invention. A liquid droplet introducing tank 3H of the present embodiment differs from the previously described embodiments in that it has a hydrophobic region 36. The hydrophobic region 36 is formed in a portion of the top surface 31a that surrounds the opening 32. The hydrophobic region 36 is a portion that demonstrates stronger hydrophobicity with respect to liquid droplets Dr than portions of the top surface 31a other than the hydrophobic region 36, and is formed by carrying out hydrophobic treatment on a portion of the top surface 31a. This type of configuration also makes it possible to prevent the opening 32 from being blocked by the liquid droplets Dr.

The liquid droplet introducing tank and analyzing device relating to the present invention are limited to the previously described embodiments. The design of the specific configuration of each portion of the liquid droplet introducing tank and analyzing device relating to the present invention may be altered in various ways.

The shapes of the tank body 31 and the injection hole 32 are not limited to the shapes having a circular cross-section described above, but rather are only required to have a shape that is suitable for injection of liquid droplets Dr. Although arranging the relative locations of the tank body 31 and the injection hole 32 such that a portion of the side surface 31c and a portion of the inner surface 32a lie within the same plane as previously described is suitable for allowing the liquid droplets Dr to promptly contact the side surface 31c, the present invention is not limited thereto. The liquid droplets Dr can be promoted to contact the side surface 31c if the center of the injection hole 32 is arranged to be closer to the side surface 31c than the center of the tank body 31 (top surface 31a). The drying reagent 4 is not limited to the so-called salt reagent previously described, but rather is only required to be that which demonstrates satisfactory hydrophilicity with respect to the liquid droplets Dr. In addition, means for providing a hydrophilic region as referred to in the present invention is not limited to the formation of the drying reagent 4, but rather hydrophilic treatment may also be carried out on a portion of the bottom surface 31b, for example. So-called ultraviolet treatment, by which a surface is modified by using ultraviolet light, may also be used for the hydrophilic treatment. Applications of the liquid droplet injections tanks 3A to 3F are not limited to being provided in the analyzer analyzing device A, but rather include use in all types of devices into which liquid droplets Dr are injected. The analyzing device A relating to the present invention is not limited to blood analysis applications, but rather can naturally also be widely used in applications such as using injected liquid droplets Dr to make dilutions or using liquid droplets Dr directly as specimens, as well as in applications other than so-called medical applications.

The invention claimed is:

1. A liquid droplet introducing tank, comprising:
a tank body formed by mutually opposing first and second surfaces, and a side surface that spreads out in a direction in which the first and the second surfaces are spaced apart the tank body having a circular cross-section; and
an injection hole that is opened in the first surface;
wherein liquid droplets are introduced from the injection hole, wherein a center of the injection hole is closer to the side surface than a center of the first surface,
wherein a plurality of hydrophilic regions that demonstrate hydrophilicity greater than that of other portions are formed on at least one of the first surface, the second surface and the side surface each of the plurality of hydrophilic regions as a whole being smaller in size than the injection hole, and
wherein the plurality of hydrophilic regions include hydrophilic regions spaced apart from each other and disposed along the side surface.

2. The liquid droplet introducing tank according to claim 1, wherein a portion of an inner surface of the injection hole and a portion of the side surface are flush with each other.

3. The liquid droplet introducing tank according to claim 1, wherein the plurality of hydrophilic regions are made of a drying reagent or a liquid.

4. The liquid droplet introducing tank according to claim 1, wherein at least one of the first and the second surfaces is formed with a resistance boundary line that generates a resistance force against progression of liquid droplets beyond the resistance boundary line, and that extends from a location that overlaps with the injection hole to a location that does not overlap with the injection hole when viewed, in the direction in which the first and the second surfaces are spaced apart.

5. The liquid droplet introducing tank according to claim 1, wherein at least a portion of the side surface is not perpendicular to at least one of the first and the second surfaces.

6. The liquid droplet introducing tank according to claim 1, wherein the first and the second surfaces are not parallel to each other.

7. The liquid droplet introducing tank according to claim 1, wherein the first surface is further formed with a rib that surrounds at least a portion of the injection hole and protrudes toward the second surface.

8. The liquid droplet introducing tank according to claim 1, wherein the first surface is provided with a swelling member that surrounds at least a portion of the injection hole and swells by absorbing a portion of the liquid droplets.

9. The liquid droplet introducing tank according to claim 1, wherein the first surface is formed with a hydrophobic region that surrounds at least a portion of the injection hole.

\* \* \* \* \*